United States Patent [19]

Asai et al.

[11] 4,409,147
[45] Oct. 11, 1983

[54] CARBAPENEM COMPOUNDS AND THEIR PRODUCTION

[75] Inventors: Mitsuko Asai, Takatsuki; Susumu Shinagawa, Higashiosaka; Akira Imada, Nishinomiya, all of Japan

[73] Assignee: Takeda Chemical Industries, Ltd., Osaka, Japan

[21] Appl. No.: 236,310

[22] Filed: Feb. 20, 1981

[30] Foreign Application Priority Data

Mar. 10, 1980 [JP] Japan .................................. 55-30701
Mar. 10, 1980 [JP] Japan .................................. 55-30702

[51] Int. Cl.³ .......................................... C07D 487/04
[52] U.S. Cl. .............................. 260/245.2 T; 424/274
[58] Field of Search ................................. 260/245.2 T

[56] References Cited

U.S. PATENT DOCUMENTS

| | | | |
|---|---|---|---|
| 4,141,986 | 2/1979 | Cassidy et al. | 260/245.2 T |
| 4,162,323 | 7/1979 | Kahan | 260/245.2 T |
| 4,189,473 | 2/1980 | Cole et al. | 260/245.2 T |
| 4,210,661 | 7/1980 | Ponsford et al. | 260/245.2 T |
| 4,223,038 | 9/1980 | Smale | 260/245.2 T |
| 4,341,705 | 7/1982 | Shih | 260/245.2 T |
| 4,341,706 | 7/1982 | Christensen et al. | 260/245.2 T |

FOREIGN PATENT DOCUMENTS

| | | | |
|---|---|---|---|
| 8497 | 3/1980 | European Pat. Off. | 260/245.2 T |
| 1483142 | 3/1976 | United Kingdom | 260/245.2 T |

OTHER PUBLICATIONS

Harada et al.; J. of Antibiotics; vol. 33, pp. 1425–1430, (12/1980).

*Primary Examiner*—Mary C. Lee
*Attorney, Agent, or Firm*—Wenderoth, Lind & Ponack

[57] ABSTRACT

Novel carbapenem compounds, which are shown by the formula (I):

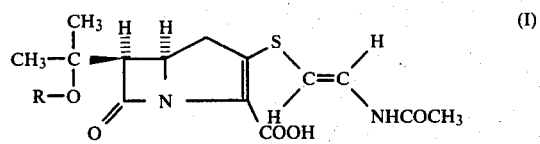

wherein R is $-SO_3H$ or hydrogen, or a physiologically acceptable salt thereof, are useful as a bactericide or disinfectant, and also produce a synergistic effect with penicillin and/or cephalosporin antibiotic agents.

The compound of the formula (I) can be produced by subjecting to reduction reaction a compound of the formula:

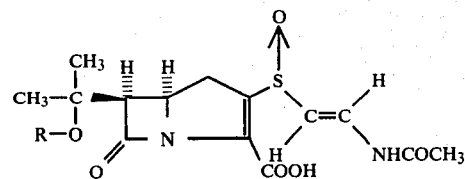

wherein R has the same meaning as defined above, or a salt thereof.

2 Claims, No Drawings

CARBAPENEM COMPOUNDS AND THEIR PRODUCTION

The present invention relates to novel carbapenem compounds of the formula (I)

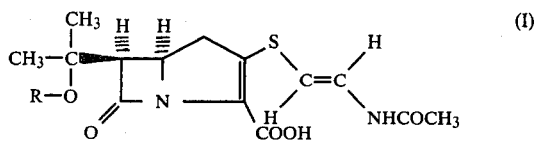

wherein R is —SO$_3$H or hydrogen, or a physiologically acceptable salt thereof, which are of value as an antimicrobial agent.

The object compounds of the formula (I) or a physiologically acceptable salt thereof [hereinafter sometimes referred to as "compound (I)"] can be produced by subjecting to reduction reaction a compound of the formula (II):

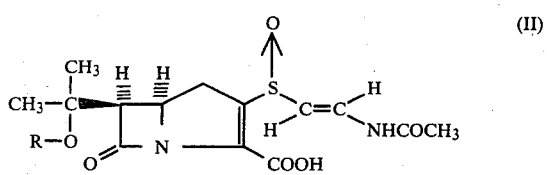

wherein R has the same meaning as defined above, or a salt thereof [hereinafter sometimes referred to as "compound (II)"].

In the formula (II), the compound in which R is —SO$_3$H was designated as Antibiotic C-19393S$_2$ and the compound in which R is hydrogen was designated as Antibiotic C-19393H$_2$.

As examples of the above reduction reaction there may be mentioned catalytic reduction reaction. In such catalytic reduction reaction, the conventional procedures may be adopted, and as examples of the catalyst there may be mentioned platinum catalysts such as platinum wire, platinum sponge, platinum black, platinum oxide and colloidal platinum, palladium catalysts such as palladium sponge, palladium black, palladium oxide, palladium barium sulfate, palladium barium carbonate, palladium carbon, palladium silica gel and colloidal palladium, and nickel catalysts such as reduced nickel, nickel oxide, Raney nickel and Urushibara nickel. Examples of the solvent employable include solvents capable of dissolving the starting compound (II), such as water and mixtures of water and polar organic solvents, e.g. dioxane, tetrahydrofuran, dimethylformamide, methanol, ethanol, propanol, etc. The reaction is preferably conducted at 0° to 50° C. under 1 to 2 atmospheric pressure of hydrogen. After the conclusion of the reaction, the objective compound (I) of the present invention can be easily separated from unreacted starting materials or reaction by-products by removing the catalyst from the reaction mixture by a suitable procedure such as filtration, and subjecting the mixture to column chromatography which comprises adsorbing on a polystyrene adsorptive resin such as Amberlite XAD-II resin (Rohm & Haas Co., U.S.A.) and eluting with water or aqueous alcohol as an eluting solvent. Typically, detection of the fraction eluted from XAD-II resin is carried out by injecting a portion of said fraction as a sample into a system of high performance liquid chromatography utilizing a 254 nm UV detector and Microbondapak C$_{18}$ (Waters Associates Inc., U.S.A.).

Salts of the compounds (I) and (II) include, for example, those with alkali metals such as sodium, potassium and lithium, those with alkaline earth metals such as magnesium, calcium and barium, and those with organic amines such as trimethylamine, triethylamine and pyridine.

The starting compound (II) of the present invention is produced, for example, by cultivating Streptomyces sp. strain C-19393 (FERM-P No. 4774, IFO 13886, ATCC 31486, NRRL 15037) in a medium containing nutrients which the microorganism may utilize, and is referred to as Antibiotic C-19393 S$_2$ and H$_2$ [German Patent Laid-open (Offenlegungsschrift) No. 30 03 624].

Antimicrobial spectrum of the compound of the formula (I) wherein R is —SO$_3$H as obtained in Example I is as shown in Table 1.

TABLE 1

| Test organism | Minimal inhibitory concentration (μg/ml) |
|---|---|
| Escherichia coli NIHJ | 6.25 |
| Salmonella typhimurium IFO 12529 | 6.25 |
| Klebsiella pneumoniae IFO 3318 | 6.25 |
| Proteus vulgaris IFO 3988 | 25 |
| Proteus mirabilis ATCC 21100 | 25 |
| Serratia marcescens IFO 12648 | 12.5 |
| Alcaligenes faecalis IFO 13111 | >25 |
| Pseudomonas aeruginosa IFO 3080 | >25 |
| Comamonas terrigena IFO 13299 | 6.25 |
| Staphylococcus aureus 209P | 12.5 |
| Sarcina lutea IFO 3232 | 3.13 |
| Bacillus subtilis PCI 219 | 6.25 |
| Bacillus cereus FDA 5 | >25 |

(Note) Medium: Bouillon agar

Antimicrobial spectrum of the compound of the formula (I) wherein R is hydrogen as obtained in Example 2 is as shown in Table 2.

TABLE 2

| Test organism | Minimal inhibitory concentration (μg/ml) |
|---|---|
| Escherichia coli NIHJ | 0.31 |
| Salmonella typhimurium IFO 12529 | 0.31 |
| Klebsiella pneumoniae IFO 3318 | 0.31 |
| Proteus vulgaris IFO 3988 | >10 |
| Proteus mirabilis ATCC 21100 | 2.5 |
| Serratia marcescens IFO 12648 | 1.25 |
| Alcaligenes faecalis IFO 13111 | 10 |
| Pseudomonas aerugionosa IFO 3080 | >10 |
| Comamonas terrigena IFO 13299 | 0.31 |
| Staphylococcus aureus 209P | 2.5 |
| Sarcina lutea IFO 3232 | 0.62 |
| Bacillus subtilis PCI 219 | 0.31 |
| Bacillus cereus FDA 5 | >10 |

(Note) Medium: Bouillon agar.

The compound (I) obtained according to the present invention, as is obvious from the above antimicrobial spectrum, exhibit antimicrobial activity against gram-positive and gram-negative bacteria. Therefore, the compound (I) can be used for the treatment of bacterial infections in mammals (e.g. mouse, rat, dog, human being, etc.) and domestic animals (e.g. domestic fowl, duck, etc.)

To use the compound (I) as an agent for treating, for example, E. coli infections, the compound (I) is dissolved in physiological saline solution to prepare an injectable solution which can be administered parenterally, e.g., subcutaneously or intramuscularly at a dose of 0.1 to 200 mg/kg/day, preferably 1 to 50 mg/kg/day.

Also, for oral administration, the compound (I) is blended with lactose and encapsulated to prepare a capsule preparation which can be administered at a dose of 1 to 500 mg/kg/day, preferably 5 to 200 mg/kg/day.

Further, the compound (I) obtained in accordance with the present invention can be used as a disinfectant. For example, a liquid preparation which can be prepared by dissolving the compound (I) in distilled water at a concentration of 0.01 to 1.0 w/v % or an ointment containing 0.5 to 50 mg, preferably 2 to 20 mg, the compound (I) per 1 g of white petrolatum or lanolin as a base can be used as a bactericide or disinfectant for hands, legs, eyes, ears, etc. of the above animals.

The compound (I) exhibit a beta-lactamase inhibiting activity and, therefore, markedly increase the sensitivity of penicillin- or cephalosporin-resistant bacteria to ampicillin or cefotiam due to its ability to produce beta-lactamase. Accordingly, the compound (I) can be used for treatment of infections in mammals (for example, mouse, rat, dog, human being) and avian species (for example, domestic fowl, duck), in particular, bacterial infections due to beta-lactam antibiotic-resistant bacteria, in combination with penicillin or cephalosporin antibiotics.

When the compound (I) is used in combination with other beta-lactam type agents for the treatment of infections by, for example, beta-lactam antibiotic-resistant *E. coli*, equal amounts of the compound (I) and ampicillin are dissolved in physiological saline to prepare an injectable solution which can be administered parenterally, e.g., subcutaneously or intramuscularly, at a dose of 0.1 to 20 mg/kg/day, preferably 0.5 to 5 mg/kg/day. The compound (I) can also be administered orally at a dose of 1 to 200 mg/kg/day, preferably 5 to 100 mg/kg/day as capsules each containing an equal proportion of the compound (I) and cephalexin.

When the compound (I) is used as a disinfectant, a liquid preparation, for example, an aqueous solution containing the compound (I) at a concentration of 0.1 to 10 w/v % and benzylpenicillin at a concentration of 0.1 to 1.0 w/v %, or an ointment containing 5 to 20 mg of the compound (I) and 5 to 20 mg of benzylpenicillin per 1 g of white petrolatum or lanolin as a base can be used as a bactericide or disinfectant for hands, legs, eyes, ears, etc. of the above animals.

The compound (I) is also expected to be very useful as an intermediate for the synthesis of novel types of pharmaceuticals. The compounds of the present invention are stable in aqueous solution in a neutral pH region.

The following reference examples, and examples illustrate in more particular the practice of the present invention, but are not limitative of this invention. The term "percent" in the reference example designates weight/volume %, unless otherwise specified.

REFERENCE EXAMPLE 1

A culture of Streptomyces sp. strain C-19393 (IFO 13886, ATCC 31486) was grown on 200 ml of a medium comprised of 2% oatmeal, 2% tomato paste, 0.2% bovril (manufactured by Bovril, England) and 2% agar (pH 7.0) charged into a 1 l Erlenmeyer flask to obtain spores. The resulting spores were then suspended in sterile water at a concentration of $1.2 \times 10^8$ living cells/ml. The spore suspension was diluted with sterile water to a volume of 10 times the original volume and 1 ml of the diluted suspension was used to inoculate 40 ml of a seed medium in a 200 ml Erlenmeyer flask. The inoculated seed medium was then cultivated on a rotatory shaker at 28° C. for 2 days. The resulting culture was used to inoculate 500 ml of a seed culture medium charged into a 2 l Sakaguchi shake flask and the inoculated seed medium was cultivated on a reciprocating shaker at 28° C. for 2 days. The seed culture thus obtained was transferred to a 50 l stainless steel fermentation tank containing 30 l of a seed medium containing 15 ml of Actocol (Takeda Chemical Industries, Ltd., Japan) and cultivated at 28° C. for 3 days, with aeration at 30 l/minute and agitation at 280 r.p.m. The culture broth was transferred to a 2 m³ content fermentation tank containing 1.2 m³ of a main culture medium and cultivated at 30° C. for 5 days, with aeration at 840 l/minute and agitation at 180 r.p.m. The seed medium used above was composed of 20 g of glucose, 30 g of soluble starch, 10 g of raw soybean meal, 10 g of corn steep liquor, 5 g of Polypepton (Daigo Nutritive Chemicals, Ltd., Japan), 3 g of sodium chloride and 5 g of precipitated calcium carbonate relative to 1 l of the medium which had been adjusted to a pH of 7.0 prior to sterilization, and the main culture medium used above was composed of 30 g of glucose, 30 g of soluble starch, 15 g of defatted soybean meal, 15 g of cottonseed flour, 0.25 g of potassium dihydrogen phosphate, 0.6 g of potassium monohydrogen phosphate, 0.002 g of cobalt chloride and 0.5 g of Actocol per 1 l of the medium which had been adjusted to a pH of 7.0 prior to sterilization. All the media used above were steam-sterilized at 120° C. for 20 minutes.

The fermentation broth thus obtained was filtered with Hyflo-Supercel (Johnes Manville Co., U.S.A.) to obtain 1230 l of a filtrate which was then adjusted to pH 6.3 and passed through a column packed with 100 l of activated carbon. Then, C-19393S$_2$ and H$_2$ were eluted from the column with 300 l of water and 700 l of 7% aqueous isobutanol, respectively. The eluate containing C-19393S$_2$ was passed through a column of Dowex 1×2 (Dow and Chemical Co., U.S.A., Cl⁻ form, 2 l), and the column was washed with 6 l of water and eluted with 32 l of 5% aqueous sodium chloride. The eluate was adjusted to pH 5 and passed through a column packed with 4 l of activated carbon. After washing with 12 l of water, the desired antibiotic was eluted with 7 l of 8% aqueous isobutanol and 12 l of isobutanol: N/20 aqueous ammonia (8:92), and the eluate was concentrated to a volume of 150 ml under reduced pressure. 1350 ml of methanol was added to the concentrate and the precipitate thus formed was removed by filtration. The filtrate was concentrated to a volume of 200 ml, and passed through a column packed with 300 ml of DEAE-Sephadex A-25 (Pharmacia Co., Sweden, Cl⁻ form). The column was washed successively with 0.1 M and 0.2 M aqueous sodium chloride solutions (each 900 ml) and, thereafter, the desired antibiotic substance was eluted with 1500 ml of 0.4 M aqueous sodium chloride. The eluate was adjusted to pH 5 and passed through a column packed with 500 ml of activated carbon. After washing with 1.5 l of water, the column was eluted with 2.5 l of isobutanol:N/20 aqueous ammonia (8:92), and the eluate was concentrated to dryness and acetone was added to the residue to obtain 2.4 g of a pale yellow powder. After dissolving the resulting powder in a small amount of water, the solution was passed through a column packed with 1.2 l of Amberlite XAD-II (100 to 200 mesh) and eluted fractionally with water. The fractions which showed antibiotic activity were pooled and concentrated, and the concentrate was passed through a column packed with 200 ml of QAE- Sephadex A-25 (Pharmacia Co., Sweden, Cl⁻ form). After washing with 600 ml of 0.1 M aqueous sodium chloride, the column was eluted with 1.2 l of 0.2 M aqueous sodium chloride. The eluate was adjusted to pH 5 and passed through a column packed with 600 ml of activated carbon. After washing the column with 1.8 l of water, the column was eluted with 3 l of isobutanol:N/20 aqueous ammonia (8:92). The eluate was concentrated to dryness and acetone was added to the residue to obtain 1.07 g of a powdery product. A 620 mg portion of the powder thus obtained was dissolved in a small amount of water and the solution was passed through a column packed with 360 ml of Amberlite XAD-II (100 to 200 mesh). The column was then eluted and fractionated with water, and each of the fractions which revealed antibiotic activity was subjected to analysis by liquid chromatography as described above. The fractions which showed a single peak were pooled and concentrated to dryness, and acetone was added to the concentrate to obtain 136 mg of Antibiotic C-19393S₂ disodium salt as a white powdery product.

Specific rotation of the product was $[\alpha]_D^{22} - 152° \pm 15°$ (C=0.5, water).

REFERENCE EXAMPLE 2

The eluate of C-19393H₂ obtained in Reference Example 1 was passed through a column of Dowex 1×2 (Cl⁻ form, 12 l), and the column was washed with 6 l of water and eluted with 180 l of 5% aqueous sodium chloride. The eluate was passed through a column packed with 25 l of activated carbon. After washing with 75 l of water, the desired antibiotic was eluted with 175 l of isobutanol:water (7:93), and the eluate was concentrated to a volume of 2 to 3 l under reduced pressure. 15 l of methanol was added to the concentrate and the precipitate thus formed was removed by filtration. The filtrate was concentrated to a volume of 2 l, and passed through a column packed with 5 l of Diaion High Porous Type Resin HP-20(Mitsubishi Chemical Industries, Japan, hereinafter referred to as "Diaion HP-20", 50 mesh). The column was then eluted and fractionated with 5 l of water, then with 10 l of methanol:water (1:9). The active fractions were pooled and concentrated, and the concentrate was passed through a column packed with 3 l of DEAE-Sephadex A-25 (Cl⁻ form). The column was washed with 9 l of 0.02 M aqueous sodium chloride and the desired antibiotic was eluted and fractionated with 12 l of 0.05 M aqueous sodium chloride. The active fractions were passed through a column packed with 2 l of Diaion HP-20 (50 mesh) which had been treated with 4 l of aqueous sodium chloride and, after washing with 10 l of 5% aqueous sodium chloride, the active principle was eluted and fractionated with 10 l of methanol:5% aqueous sodium chloride (5:95) and 10 l of methanol:5% aqueous sodium chloride (1:9). The active fractions were passed through a column packed with 500 ml of activated carbon and, after washing with 1.5 l of water, eluted with 2.5 l of 7% aqueous isobutanol. The eluate was concentrated, and the concentrate was passed through a column packed with 1 l of Diaion HP-20 (50 to 100 mesh) and eluted and fractionated with water. The fractions having antibiotic activity were pooled and concentrated, and the concentrate was passed through a column packed with 200 ml of QAE-Sephadex A-25 (Cl⁻ form) which had been treated with 400 ml of 0.02 M aqueous solution of sodium chloride. The column was then successively eluted with 0.02 M, 0.03 M and 0.04 M aqueous sodium chloride solutions (each 1 liter). The active fractions were passed through a column packed with 200 ml of activated carbon and, after washing with 0.6 l of water, eluted with 1 l of 7% aqueous isobutanol. The eluate was concentrated, and propanol was added to the concentrate to prepare 90% aqueous propanol which was then subjected to an Avicel column chromatography which had been treated with 90% aqueous propanol. The column was eluted with 90% aqueous propanol. The active fractions were concentrated and the concentrate was subjected to column chromatography on 350 ml of Amberlite XAD-II (100 to 200 mesh) and the column was eluted with water. The active fractions were concentrated and the concentrate was subjected to a preparative high performance liquid chromatography using RP-18(E.Merck & Co., West Germany) as a carrier and eluted with 10% methanol in 0.02 M phosphate buffer (pH 6.3). The active fractions were passed through a column packed with 40 ml of Diaion HP-20 (100 to 200 mesh) and fractionally eluted with water. Each of the fractions which revealed antimicrobial activity was subjected to the analysis of liquid chromatography as described above. The fractions which showed a single peak were pooled and freeze-dried to obtain 12 mg of C-19393H₂ sodium salt as a white powdery product.

Specific rotation of the product was $[\alpha]_D^{26} - 134°$ (C=0.156, water).

EXAMPLE 1

Crude powder (30% of purity, 60 mg) of Antibiotic C-19393S₂ disodium salt was dissolved in 10% aqueous methanol (20 ml), and the resulting solution was added to a mixture of 10% aqueous methanol (10 ml) and 10% palladium-carbon (20 mg) into which hydrogen had been introduced in advance for 30 minutes. Then, hydrogen was introduced into the resultant mixture at room temperature under 1 atmospheric pressure for 3 hours to carry out reduction, and the catalyst was then filtered out, followed by concentrating the filtrate under vacuum to 2 ml of volume. The concentrated solution was flown through a column (50 ml) of Amberlite XAD-II (100 to 200 mesh), and the objective compound was adsorbed on the adsorbent and then eluted with water. The fractions from 45 ml to 150 ml which contained the objective compound were collected and lyophilized, whereby there was obtained 7.3 mg of powder of disodium [5R, 6R]-3-[(E)-2-acetamidoethenylthio]-6-[1-(hydroxysulfonyloxy)-1-methylethyl]-7-oxo-1-azabicyclo[3,2,0]hepto-2-en-2-carboxylate.

UV: λmax(H₂O) 228 and 309 nm

IR: νmax(KBr) 1760, 1620, 1240, 1050 cm⁻¹

Thin layer chromatography [Cellulose f (Tokyo Kasei Co., Ltd.)]: Rf=0.65 (solvent system: propanol:water=4:1)

High performance liquid chromatography (Waters Associates Inc.): Rt=4.4 min. [Microbondapak C₁₈/14% methanol-0.02 M-phosphate buffer (pH 6.3), 2 ml/min/cm (200 psi)], wherein Rt of the starting compound under the same conditions was 2.2 min.

NMR; δ(100 MHz, D₂O, TMS): 1.63(3H,S,C₈—CH₃), 1.70(3H,S,C₈—CH₃), 2.10(3H,S,COCH₃), 3.05(1H,dd,J=10,19,C₄—H), 3.82 (1H,dd,10.5,19,C₄—H), 3.88(1H,d,J=6,C₆—H), 4.20(1H,m,C₅—H), 6.10(1H,d,J=14,N—CH=), 7.20(1H,d,S—CH=).

EXAMPLE 2

Crude powder (30% of purity, 8 mg) of Antibiotic C-19393 H₂ sodium salt was dissolved in 10% aqueous methanol (10 ml), and the solution was added to a mixture of 10% aqueous methanol (10 ml) and 10% palladium-carbon (20 mg) into which hydrogen had been introduced in advance for 30 minutes. Then, hydrogen was further introduced into the resultant mixture at room temperature under 1 atmospheric pressure for 3 hours to carry out reduction, and the catalyst was then filtered out, followed by concentrating the filtrate under vacuum to 2 ml of volume. The concentrated solution was passed through a column (10 ml) of Amberlite XAD-II (100 to 200 mesh), and the objective compound was adsorbed on the adsorbent. After the column was washed with water (50 ml), elution was carried out with 20% methanol-water, and the fractions containing the objective compound were collected. Methanol of the active fractions was distilled off and the residue was freeze dried, thereby yielding 1.0 mg of powder of sodium [5R, 6R]-3-[(E)-2-acetamidethenyl-thio]-6-[1-hydroxy-1-methylethyl]-7-oxo-1-azabicyclo[3,2,0]hepto-2-en-2-carboxylate.

UV: λmax (H₂O) 229 and 310 nm
IR: νmax (KBr) 1760, 1620 cm$^{-1}$
Thin layer chromatography [Cellulose f (Tokyo Kasei Co. Ltd.)]: Rf=0.87
(Solvent system: propanol:water=4:1)
High performance liquid chromatography (Manufactured by Waters Associates Inc., U.S.A.): Rt=8.2 min. [microbondapak C₁₈/14% methanol-0.02 M phosphate buffer (pH 6.3), 2 ml/min/cm (2000 psi)], wherein Rt of the starting compound under the same conditions was 4.3 min.

NMR: δ(100 MHz, D₂O, TMS): 1.33(3H,s,C₈—C$\underline{H}$₃), 1.44(3H,s,C₈—C$\underline{H}$₃), 2.10(3H,s,COC$\underline{H}$₃), 3.03(1H,dd,J=10,19,C₄—$\underline{H}$), 3.85(1H,dd,J=10.5,19,C₄—$\underline{H}$), 3.72(1H,d,J=6,C₆—$\underline{H}$), 4.28(1H,m,C₅—$\underline{H}$), 6.10(1H,d,J=14,N—C$\underline{H}$=), 7.20(1H,d,S—C$\underline{H}$=)

What we claim is:
1. A compound of the formula:

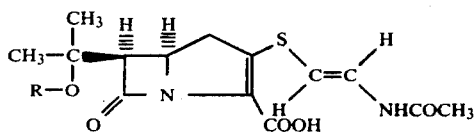

wherein R is —SO₃H, or a physiologically acceptable salt thereof.

2. A method for production of a compound of the formula:

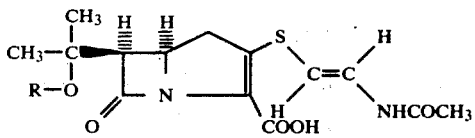

wherein R is —SO₃H or hydrogen, or a physiologically acceptable salt thereof, which comprises subjecting to catalytic reduction reaction a compound of the formula:

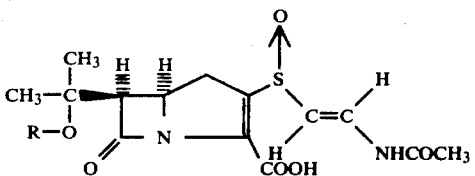

wherein R has the same meaning as defined above, or a salt thereof.

* * * * *